United States Patent [19]
Goldrath

[11] Patent Number: 5,330,488
[45] Date of Patent: Jul. 19, 1994

[54] VERRES NEEDLE SUTURING KIT

[76] Inventor: Milton H. Goldrath, 31074 Oakleaf, Franklin, Mich. 48025

[21] Appl. No.: 46,207

[22] Filed: Apr. 9, 1993

Related U.S. Application Data

[63] Continuation-in-part of Ser. No. 36,074, Mar. 23, 1993.

[51] Int. Cl.$^5$ ............................................. A61B 17/00
[52] U.S. Cl. ................................. 606/148; 606/139; 606/223; 604/158; 604/164; 604/170
[58] Field of Search ....................... 606/110–113, 606/103, 139, 144, 148, 170, 181, 184, 185, 187, 189, 223; 604/158, 161, 164, 167, 170

[56] References Cited

U.S. PATENT DOCUMENTS

| | | | |
|---|---|---|---|
| 480,870 | 8/1892 | Harris | 606/113 |
| 2,416,260 | 2/1947 | Karle | 606/148 |
| 2,630,803 | 3/1953 | Baran | 604/158 |
| 3,871,379 | 3/1975 | Clarke | |
| 4,224,947 | 9/1980 | Fukuda | |
| 4,598,699 | 7/1986 | Garren et al. | 606/185 |
| 4,808,168 | 2/1989 | Warring | 604/170 |
| 4,935,027 | 6/1990 | Yoon | 606/146 |
| 5,015,250 | 5/1991 | Foster | 606/147 |
| 5,152,769 | 10/1992 | Baber | 606/145 |
| 5,158,561 | 10/1992 | Rydell et al. | 606/110 |
| 5,183,465 | 2/1993 | Xanthakos et al. | 604/108 |

FOREIGN PATENT DOCUMENTS

WO90/06783  6/1990  PCT Int'l Appl. .............. 604/164

Primary Examiner—Stephen C. Pellegrino
Assistant Examiner—Jeffrey A. Schmidt
Attorney, Agent, or Firm—Krass & Young

[57] ABSTRACT

A Verres needle suturing device. The spring loaded probe of a Verres needle assembly is modified to include an angled guide for guiding the end of a piece of suture material from the channel of the probe out of the opening of the probe so that it can be snared by a snare introduced into the surgical site. The invention is particularly useful for relatively inaccessible surgical sites, such as result from endoscopic and laparoscopic surgery.

10 Claims, 3 Drawing Sheets

FIG-8A
FIG-8B
FIG-8C
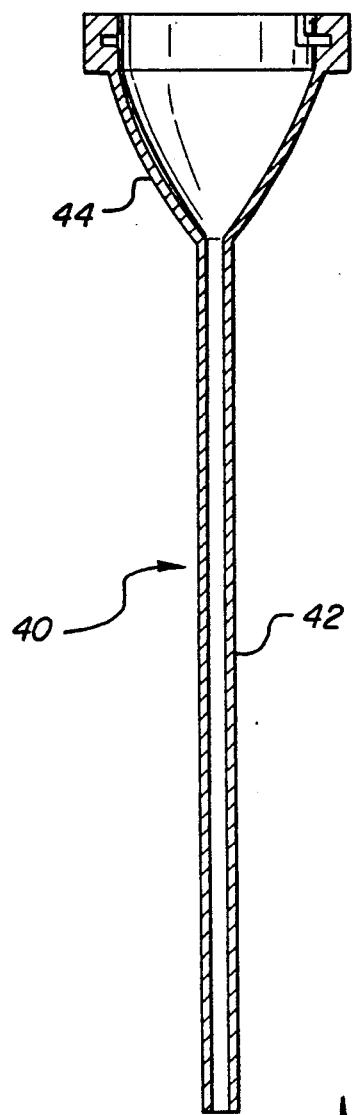
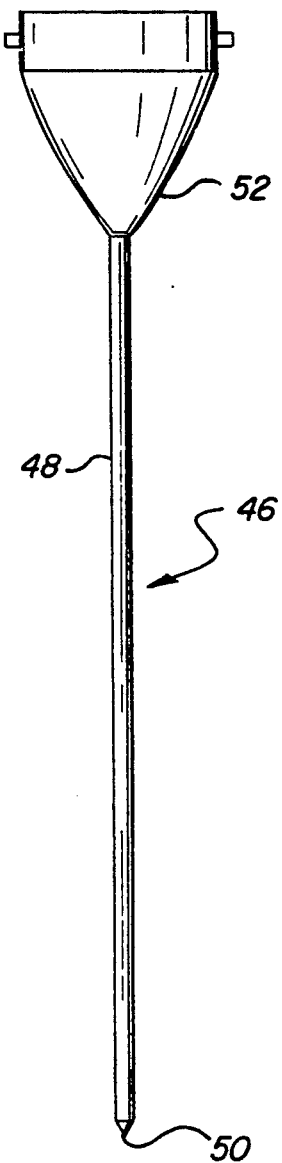
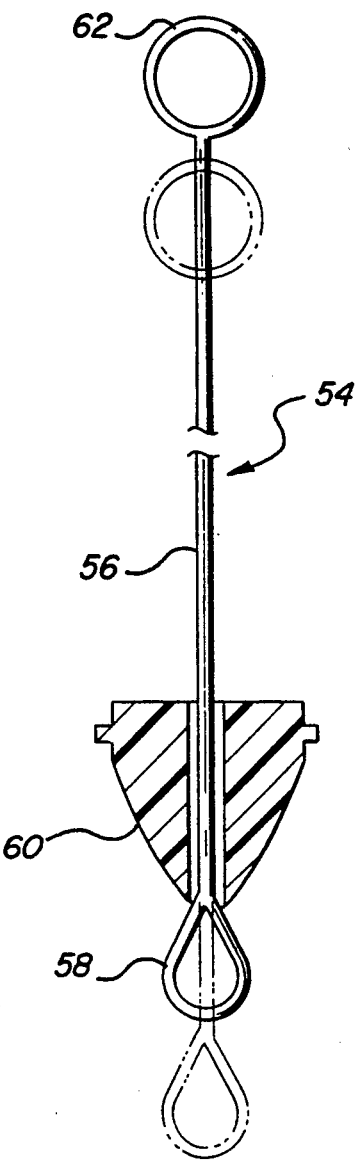
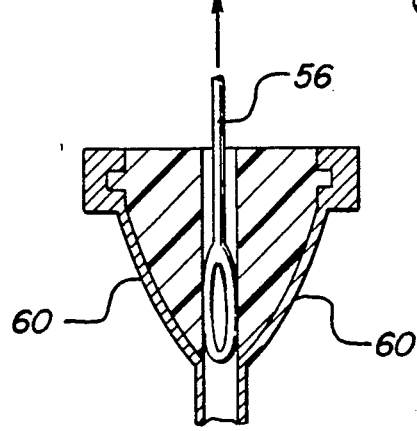
FIG-8D

VERRES NEEDLE SUTURING KIT

RELATED APPLICATION

This is a continuation in part of U.S. patent application Ser. No. 036,074, filed Mar. 23, 1993, and entitled "Verres Needle Suturing Device."

FIELD OF THE INVENTION

This invention relates to surgical instruments and, more particularly, to surgical instruments for suturing tissue at a remote surgical site.

DESCRIPTION OF THE RELEVANT PRIOR ART

A wide variety of devices are known for suturing a surgical site. These devices have been developed to assist surgeons in the suturing process, which is both time consuming and difficult due to the precision required, the number of sutures often needed, and the relative inaccessibility of many surgical sites. Access is a particular problem when suturing must be done in a "closed" surgical site, in other words, one resulting from endoscopic or laparoscopic surgery. This type of surgery is performed by using tiny instruments which are inserted through a trocar, an instrument having a hollow sheath with a sharp cutting edge disposed on its end for puncturing and cutting the external tissue over the surgical site. After the incision has been made, the various instruments may be passed through the trocar. Typically, the trocar is used to piece the external body wall of a patient so that the instruments can be passed into a body cavity of the patient for subsequent surgical manipulation.

Obviously, the "closed" surgical site which results from endoscopic and laparoscopic surgery creates particular problems in suturing since it is even more difficult to access than a typical "open" surgical site. An open surgical site results from conventional surgical methods wherein an appropriately sized surgical incision is made through the tissue of a patient and conventional surgical instruments are used. Nevertheless, even open surgical sites can present problems of access.

A number of solutions to the problems engendered by suturing in both closed and open surgical sites have been proposed. For example, U.S. Pat. No. 4,935,027 discloses a surgical suture instrument with means for remotely controllable suture material advancement. The invention provides for the continuous feed of suture material through opposed forceps jaw members between which the tissue segments are interposed to expedite the suturing process and enables suturing to be accomplished at remote internal sites of the body incident to various endoscopic procedures. While the device disclosed in the U.S. Pat. No. 4,935,027 may be effective for its stated purpose, it is also very complicated and contains numerous parts, thus rendering it very expensive to manufacture.

U.S. Pat. No. 5,015,250 discloses a needle driver instrument which is used with a trocar sheath for driving a curved suture needle to close microscopic and pelviscopic surgical sites. U.S. Pat. No. 5,152,769 discloses a suturing assembly including a suturing needle having a bore therethrough for forming an arc of thread to be grasped. A rod member secures the arc of thread formed and holds it in place, while the needle forms a second suture and secures the loop as part of the suture. U.S. Pat. No. 3,871,379 also discloses a combined laparoscopic needle and forceps for suturing and ligation of laparoscopic surgical sites. The instruments disclosed in all of these patents are especially fabricated for their special purpose and must be separately manufactured, thus increasing the expense of the surgical procedure. Furthermore, the devices disclosed in these references require that the surgeon be familiar with their operation and add to the multiplicity of instruments already typical of any surgical procedure. Both of these results are undesirable.

It would be advantageous to provide a device to aid in the suturing and ligation of relatively inaccessible surgical sites which is both simple and inexpensive to manufacture and easy to operate. It would be particularly advantageous if such a device represented a modification of existing, widely used surgical devices so as to simplify, rather than make more complex, the surgical procedure.

Verres needle assemblies have been used in the surgical field for over thirty years and are in very widespread use. While there are many commercial brands available, all Verres needle assemblies have certain elements in common: they include a trocar type hollow, cylindrical needle or sheath which terminates in a sharp cutting edge (typically angled) for piercing the external body tissue of a patient. A spring loaded, hollow, gas introducing probe is disposed inside the sheath. The probe includes a cylindrical outer surface, a blunt free end, a longitudinal channel formed through the probe, and an opening onto the outer surface proximate the blunt end of the probe. In all prior art Verres needles, the channel terminates in a blind. The probe portion of the Verres needle assembly moves between a first, extended position, wherein the blunt end projects from the surrounding sheath, to a second, retracted position, wherein the blunt end is substantially disposed inside the sheath. When the probe is in its second, retracted position, the sharp cutting edge of the sheath will cut through the patient's external tissue. On the other hand, when the probe is in its first, extended position, the blunt end will prevent the sheath cutting edge from cutting the patient's internal tissue. Typically, the probe is spring biased into its first, extended position. Thus, when an incision must be made to perform endoscopic or laparoscopic surgery, the assembly will be pushed against the patient's skin, the spring being resilient enough so that the resultant pressure will cause the probe to move to its retracted position, thus permitting the sharp edge of the sheath to pierce the patient's skin and underlying tissue. However, once the device has entered a body cavity underlying the patient's external tissue, the assembly will no longer encounter resistance, and the probe will move back to its extended position, thus preventing the sharp edge of the sheath from doing any further cutting. A Verres needle assembly also includes means for introducing a therapeutic gas into the body cavity through the channel and opening formed in the probe.

In a typical, prior art Verres needle assembly, the channel is simply a straight bore through the probe which is plugged at the tip, with a side opening out onto the cylindrical surface of the probe. Thus, the structure of the Verres needle assembly does not lend itself to introduction of surgical suture material into a surgical incision site since it is virtually impossible to thread a piece of suture material through the channel of the probe and out the side opening. Inevitably, the end of the piece of suture material simply abuts against the inside of the end of the probe and cannot be forced out the side opening.

SUMMARY OF THE INVENTION

The present invention takes advantage of the various capabilities of the Verres needle but eliminates the disadvantage noted above of the prior art Verres needle structure. The present invention is a modified Verres needle assembly which is particularly advantageous for performing suturing of relatively inaccessible surgical sites, such as closed surgical sites. The present invention accomplishes this by modifying the probe of a Verres needle assembly to include an angled guide for directing the end of a piece of suture material from the longitudinal channel of the probe out of the side opening thereof. The angled guide is in communication with both the channel and the opening, and is angled in a direction toward the opening so that the end of the piece of surgical material is directed thereout. Thus, when the piece of suture material is threaded through the modified Verres needle assembly of the present invention, instead of simply and fruitlessly poking against the blocked end of the channel, it will be directed from the channel to the opening via the angled guide.

The angle guide of the present invention may be provided in a modified Verres needle assembly in a variety of ways. For example, it may be molded in a plastic top which is simply insertable into the open end of the channel. Also, the open end of the channel may be closed off in the conventional manner, and a portion of the channel wall crimped inwardly, thus forming both angled guide and connected opening. Alternatively, the guide may be molded into the channel by filling the end of the channel with a small amount of epoxy or other filler material and allowing it to harden at an angle, thus resulting in an angled guide.

In the method of the present invention, the suturing is performed by inserting a piece of suture material into the probe channel of the modified Verres needle assembly. The suture material is threaded through the channel until the end of the piece projects through the side opening. At that point, the projecting end may simply be caught by means of snare (such as resilient loop, a hook or any suitable configuration) which is also inserted into the surgical site, preferably through a conventional trocar. After the end of the surgical material has been snared, it is then withdrawn from the surgical site, and a knot is tied by using the free ends of the surgical material thus made available. Alternatively, the snare may be inserted into the surgical site as described above, and the tip of the modified probe with the end of suturing material projecting therefrom may be inserted into the snare so that the snare will more readily capture the suture material.

The invention also includes a particular snare assembly which comprises an elongated stylet having a sharpened point at one end, and a cannula including a generally tubular passageway configured to surround at least a portion of the length of the stylet so that the sharpened point projects therefrom. The cannula is further configured to lockably engage the stylet when it is disposed within the tubular passage. The snare assembly also includes a snare shaft which comprises a generally elongated shaft configured to fit into the tubular passageway of the cannula. The shaft has a loop of a resilient material at one end thereof. The loop is normally of a diameter greater than the diameter of the tubular passageway, but it is capable of being compressed into a shape which fits into the tubular passageway. The snare shaft further includes a collar portion surrounding a portion of its length. The collar is slidable along the length of the shaft and is also configured to lockably engage the cannula.

BRIEF DESCRIPTION OF THE DRAWINGS

The following detailed description is best understood by reference to the following drawings in which:

FIGS. 8A-8D depict one configuration of snare assembly which may be used in the practice of the present invention.

DETAILED DESCRIPTION OF THE PREFERRED EMBODIMENTS

Figure 1:
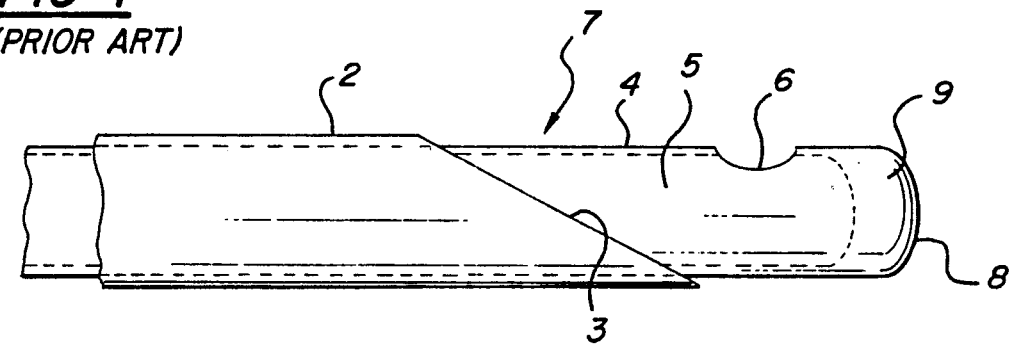
FIG. 1 shows the relevant portion of a typical, prior art Verres needle assembly.

Throughout the following detailed description, like reference numerals are used to identify the same element of the herein invention shown in multiple figures thereof. Referring now to the drawings, and in particular to FIG. 1, there is shown a portion of a typical, prior art Verres needle assembly 7. The prior art needle assembly includes a hollow, cylindrical sheath 2 terminating in an angled sharp edge 3 for puncturing the outer body tissue of a patient (not shown). A spring loaded, hollow, gas introducing probe 4 is disposed inside the hollow sheath 2 and includes a cylindrical outer surface 9, a longitudinal channel 5 formed therein, and a blunt end 8 which terminates the channel 5. An opening 6 is formed on the outer surface 9 of the probe 4 and is in communication with the channel to permit introduction of a therapeutic gas by the Verres needle assembly into internal body structures of the patient.

Like other typical prior art Verres needle assemblies, the probe 4 of the embodiment depicted in FIG. 1 is capable of moving between a first, extended position (as depicted in FIG. 1) wherein the blunt end 8 projects beyond the cutting edge 3 of the sheath 2 to a second, retracted position (not depicted) wherein the blunt end 8 is substantially disposed inside the sheath 2. A prior art Verres needle assembly is spring biased into the first, extended position but, when the cutting edge 3 is pushed against the skin of a patient undergoing laparoscopic or endoscopic surgery, the force exerted by the skin will cause the probe 4 to move to its retracted position, thereby permitting the cutting edge 3 to cut and penetrate the skin and underlying tissue. However, once these structures have been breached, and the tip of the needle assembly has penetrated into an internal body cavity of the patient, the probe 4 will no longer encounter this resistance and will move back into its first, extended position. The blunt end 8 will then protect the patient's internal body tissue from accidental trauma from the cutting edge 3.

It can readily be seen that the embodiment depicted in FIG. 1 is unsuitable for use as a suturing instrument since any attempt to thread a piece of suture material down the channel 5 will result in the end of the piece of suture material abutting against the inner surface of the blunt end of the probe. It is very difficult, if not impossible, to extract the end of a piece of suture material from the channel through the opening 6.

Figure 2:
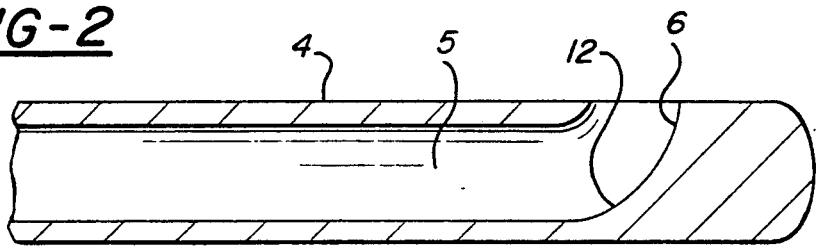
FIG. 2 is a cross-sectional view of the probe of a Verres needle assembly modified according to the present invention.

FIG. 2, which is a cross sectional view of a probe 10 modified according to the teachings of the present invention, shows that an angled guide 12 has been formed in the probe 10. The angled guide 12 connects the opening 6 with the channel 5; the angled guide 12 tapers in a direction toward the opening 6. Thus, when a piece of suture material is threaded through the channel 5 of the modified probe 10, the end of the material will be guided by the angled guide 12 out of the opening 6 where it will be readily available for suturing.

Figure 7:
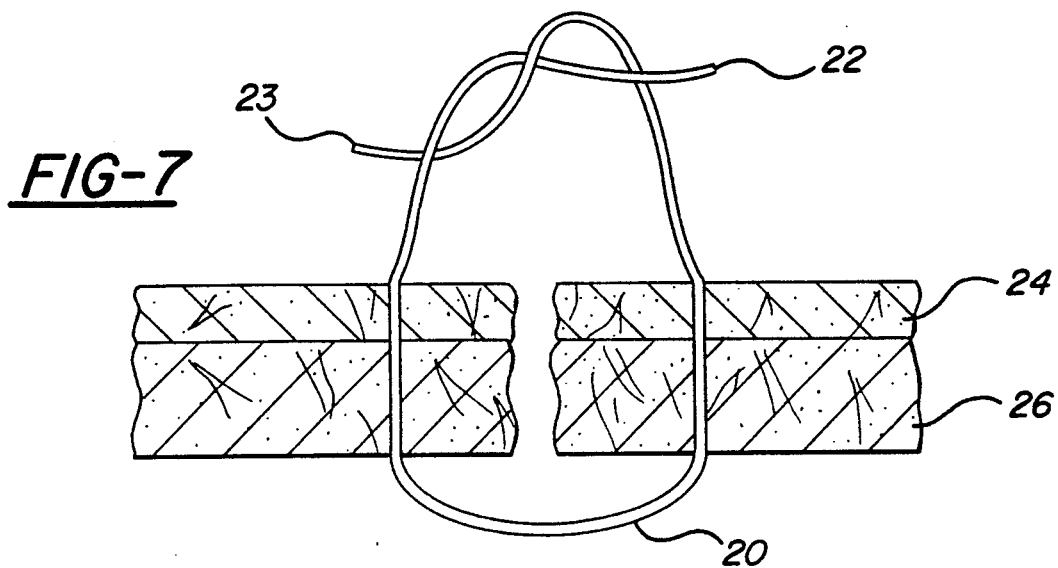
FIG. 7 shows the completion of the suture.
Figure 6:
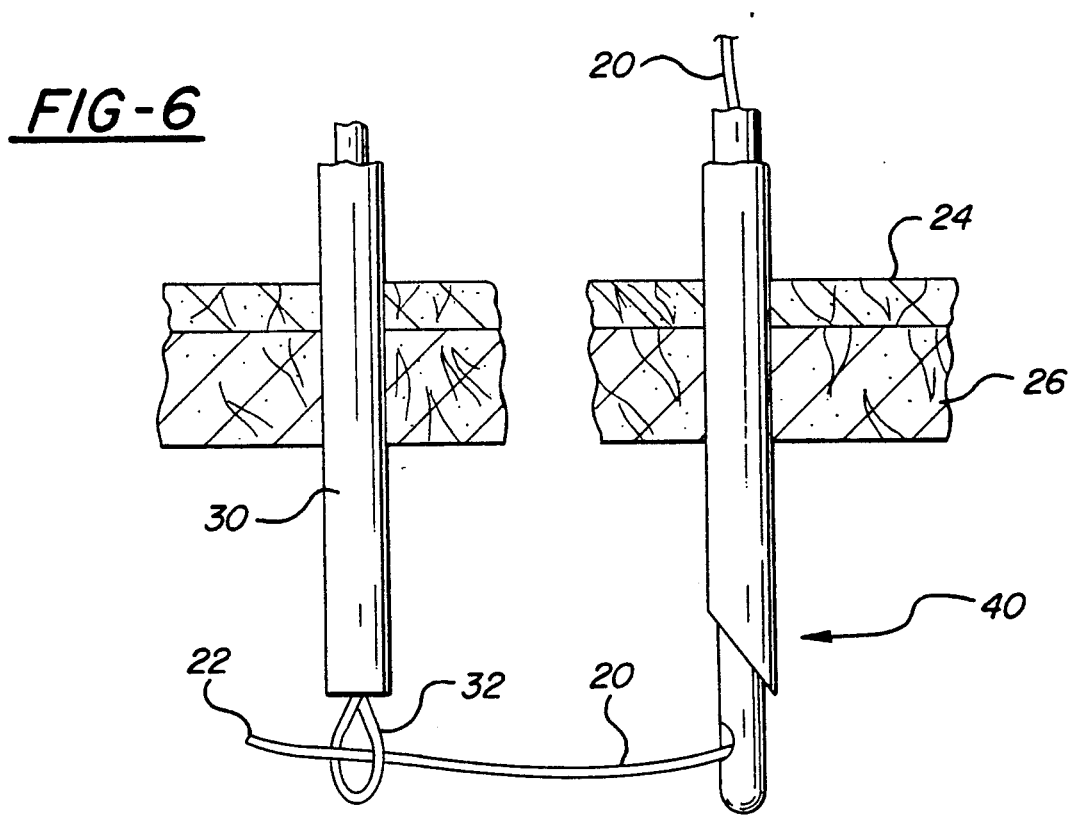
FIG. 6 shows a suture being placed according to the method of the present invention.

FIGS. 6 and 7 illustrate the method of suturing of the present invention. A Verres needle 40 modified according to the teachings of the present invention has been threaded with a piece of suture material 20 having a free end 22. The modified Verres needle 40 has a probe similar to that depicted in FIG. 2. Hence, when the piece of suture material 20 is threaded through the channel of the probe, it will be guided by the angled guide out of the opening and will emerge where it may be grasped by snare 32.

As illustrated in FIG. 6, the modified Verres needle 40 has been introduced into a surgical site through the skin 24 and underlying tissue 26 of a patient. Similarly, a trocar 30 has been introduced into the surgical site by penetrating structures 24 and 26. Snare 32 was passed into the surgical site through trocar 30. After the end 22 of the piece 20 of surgical material has been captured by snares 32, it may be withdrawn from the surgical site through the trocar 30, as has been done in FIG. 7. The modified Verres needle assembly 40 and the trocar 30 and snare 32 may then also be withdrawn from the patient's skin 24 and underlying tissues 26, thus leaving a surgical site with two projecting ends 22, 23 of suture material 20. These ends 22, 23 may then be tied off in the manner depicted in FIG. 7 to suture the surgical site.

Although the snare 32 shown in FIG. 6 is in the form of a loop, it is to be understood that the method of the present invention may be practiced with suture snares of other configurations, including hooks, clamps, etc. The important thing is that the snare be able to capture the free end of suture material introduced through the modified probe of the Verres needle. In some instances, the snare may be fabricated from a material having a shape memory. The snare, in such instances, will include a kink in its shaft proximate the loop portion and when projected from the trocar, the loop of this snare will incline toward the probe.

There are a number of configurations of snare which may be used in the practice of the present invention. FIGS. 8A–8D illustrate one particular embodiment of snare assembly which may be utilized in the present invention. The snare assembly includes a cannula 40 shown in FIG. 8A. The cannula 40 includes a generally tubular portion 42 which, in use, projects into the body of the patient, and an upper portion 44 configured to receive and retain certain components of the assembly.

Illustrated in FIG. 8B is a stylet 46 which generally comprises an elongated piercing portion 48 which terminates in a point 50. The stylet 46 further includes an upper portion 52. The elongated portion 48 of the stylet is configured to fit within the tubular portion 42 of the cannula so that the point 50 projects therefrom. The upper portion 52 of the stylet fits into the upper portion 44 of the cannula, and in the illustrated embodiment, the cannula 40 and stylet 46 lock together, by means such as a Luer lock or any other such cam lock arrangements, so as to form a rigid unit. It will be noted in the figures that the upper portion 44 of the cannula 40 is of a somewhat tapered shape, and that the upper portion 52 of the stylet 46 corresponds in shape. This tapering shape serves to guide the stylet 46 into the cannula 40; although it is to be understood that other shapes, including cylindrical shapes and the like may similarly be employed.

The snare assembly further includes a snare shaft 54 shown in FIG. 8C. The snare shaft 54 includes a shaft portion 56 which is configured to fit into the tubular portion 42 of the cannula 40. The snare shaft 54 further includes a loop portion 58, at one end of the shaft 56. This loop portion 58 is fabricated from a resilient material such as a flexible metal or polymer having a shape memory. The diameter of the loop portion 58 is preferably selected so that the loop 58 is normally of a diameter which is greater than the diameter of the tubular portion 42 of the cannula 40, but is capable of being compressed into a configuration which will permit it to pass into the tubular portion 42. The snare shaft further includes a handle 62 at the top and a collar portion 60 surrounding a portion of the length of the shaft 56. The collar portion 60 is slidable along the shaft as is illustrated herein, and it corresponds generally to the shape of the upper portion 44 of the cannula 40 and preferably includes means for locking it to the upper portion 44. In use, the collar is slid down the shaft until it compresses the loop 58 therewithin. FIG. 8D illustrates the collar 60 showing a loop 58 compressed therewithin and includes a portion of the shaft 56 projecting therefrom.

In the use of the snare assembly, the stylet portion 46 is first fitted into the cannula 40 so that the point 50 projects therefrom. The stylet 46 is locked to the cannula 40 and the two members are pushed through the patient's body wall. When used together in this manner, the stylet 46 and cannula 40 are collectively referred to as a Trochar. When the assembly has penetrated into the body cavity, the stylet 46 is unlocked from the cannula 40 and withdrawn, thereby leaving the cannula in place to provide access to the interior of the patient's body. The snare shaft 54 with the loop 58 compressed into the collar 60 is then fitted into the cannula 40 and the collar 60 locked to the cannula. The shaft 56 is then pushed downward, preferably by means of the handle 62, so as to push the loop 58 through the tubular passageway 42 and into the patient's body cavity. After the loop 58 leaves the passage 42 it springs back to its original shape. The loop then provides means for snaring the suture as noted above. When the suture is caught in the loop 58, the shaft 56 is withdrawn so as to pull the loop 58 at least partially back into the tubular passageway. The entire assembly may then be withdrawn so as to convey the suture material to the outside of the patient's body. Alternatively, the loop may be completely withdrawn from the cannula 44 and the cannula subsequently withdrawn. In some instances, it may be advantageous to merely withdraw the entire assembly through the body wall of the patient.

The snare assembly of FIGS. 8A–8D may be made of relatively small diameter so as to minimize impact of the procedure on the patient. The stylet portion 46 is made at least partially of a durable material, such as stainless steel, in order to provide a sharp point 50. The cannula 40 may be manufactured from a variety of materials, including metals such as stainless steel as well as polymeric materials. The snare shaft 54 is most preferably made from a resilient polymer such as nylon, polypropylene and the like, although it may also be fabricated from metals, preferably stainless steel, or it may comprise a composite of metal and polymeric materials.

In some cases, because the suture material 20 is relatively limp, it may be difficult to capture the free end 22 with the snare 32. Hence, in another embodiment of the method of the present invention, the method may include the step of actually inserting part of the probe of the modified Verres needle assembly into the snare so that it may more easily capture the loose end.

Figure 3:
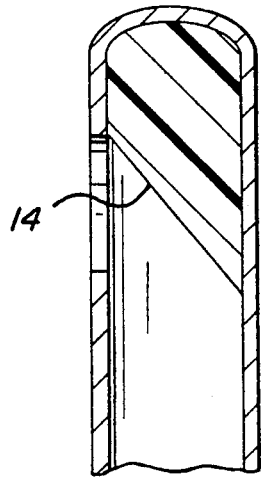
FIGS. 3, 4 and 5 are cross-sectional views which illustrate various alternate embodiments of Verres needle probes modified according to the teachings of the present invention.
Figure 4:
Figure 5:
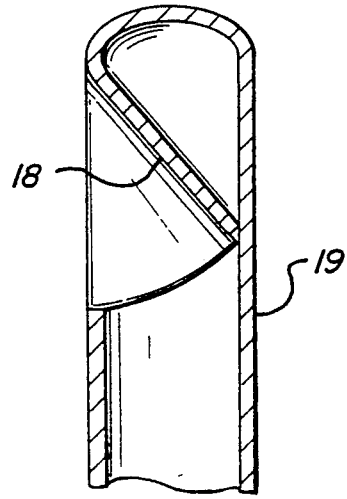

Various embodiments of the angled channel guide of the present invention are shown in FIGS. 3, 4 and 5. In FIG. 3, the angled channel guide is formed by filling the tip end of the probe with a filler material 14, such as epoxy resin. The filler 14 is allowed to harden at an angle to form the angled channel guide.

In the embodiment depicted in FIG. 4, a molded plastic tip 16 which has the angled channel guide end opening molded thereinto is simply inserted into the open channel of the probe of a Verres needle assembly. Since some commercial versions of Verres needle assembly include a plastic tip for plugging the end of the channel, this embodiment is particularly useful to modify those prior art needles.

Yet another embodiment of the present invention is shown in FIG. 5 wherein the angled channel guide is formed by crimping back a portion of sidewall 19 of the probe until it is proximate the internal surface thereof. Crimping back of portion 18 will result in formation of both an angled channel guide and an opening in one manufacturing step.

Of course, while the present invention has been depicted with reference to certain illustrated embodiments and exemplifications thereof, it is not limited by the designs depicted. One of skill in the art may, by reference to the herein specification, achieve other designs by modification of the teachings of the present invention. However, such design modifications are considered to come under the present invention, the scope of which is defined solely by the claims appended hereto and all reasonable equivalents thereof.

I claim:

1. A needle assembly kit for passing a piece of suture material into a surgical site, said kit comprising:
    a needle assembly including:
        a hollow, cylindrical sheath terminating in a sharp cutting edge for piercing external body tissue of a patient;
        and a spring loaded, hollow, gas introducing probe disposed inside said sheath and having a cylindrical outer surface, a blunt free end, a longitudinal channel formed in said probe, and an opening formed in said surface proximate said blunt free end and in communication with said channel so as to permit the passage of gas through said channel, said probe being operative to move between a first, extended position wherein said blunt tip projects from said sheath to prevent said cutting edge from cutting internal body tissue of said patient to a second, retracted position wherein said blunt tip is substantially disposed inside said sheath so as to permit said cutting edge to penetrate said tissue, said probe being biased into said first position and operative to move from said first to said second position as the needle assembly penetrates into a body cavity of said patient and:
        an angled guide connecting said channel and said opening, said guide tapering in a direction toward said opening so as, to guide an end of a piece of suture material which is treaded through said channel out of said opening for subsequent capture by a suture snare; and
    a snare assembly comprising:
        an elongated stylet having a sharpened point at one end;
        a cannula including a generally tubular passage configured to surround at least a portion of the length of the stylet so that the sharpened point projects therefrom, said cannula being further configured to lockably engage the stylet when it is disposed in the tubular passage; and
        a snare shaft comprising a generally elongated shaft configured to fit into the tubular passage of the cannula and having a loop of a resilient material at one end thereof, said loop normally being of a diameter greater than the diameter of the tubular passage, but being capable of being compressed into a shape which fits into the tubular passage, said snare shaft further including a collar portion surrounding a portion of the length of said shaft so as to be slidable therealong, said collar portion configured to lockably engage the cannula.

2. The needle assembly kit of claim 1 wherein the blunt free end includes a molded tip inserted into said channel, said tip defining said guide.

3. The needle assembly of claim 1 wherein said probe further includes a side wall, and said opening and said channel are defined by a crimped in portion of said side wall proximate said blunt end and extending in a direction opposed therefrom.

4. The needle assembly of claim 1 where said angled guide is formed by a mass of hardened filler material angularly disposed at an end of said channel.

5. The needle assembly kit of claim 1 wherein said probe further comprises a side wall and said angled guide and said opening are defined by a crimped in portion of said side wall disposed proximate said free end and extending in a longitudinal direction opposed therefrom.

6. The needle assembly kit of claim 1 wherein said angled guide is formed by a mass of hardened filler material angularly disposed at an end of said channel.

7. A snare assembly comprising:
    an elongated stylet having a sharpened point at one end;
    a cannula including a generally tubular passage configured to surround at least a portion of the length of the stylet so that the sharpened point projects therefrom, said cannula further configured to lockably engage the stylet when it is disposed in the tubular passage;
    a snare shaft comprising a generally elongated shaft configured to fit into the tubular passage of the cannula and having a loop of a resilient material at one end thereof, said loop normally being of a diameter greater than the diameter of the tubular passage, but being capable of being compressed into a shape which fits into the tubular passage, said snare shaft further including a collar portion surrounding a portion of the length of said shaft so as to be slidable therealong, said collar portion configured to lockably engage the cannula.

8. A method for suturing tissue at a surgical site comprising the steps of:

positioning a needle assembly adjacent the surgical site, the needle assembly having a hollow, cylindrical sheath terminating in a sharp cutting edge for piercing the tissue of a patient and a spring loaded hollow, probe disposed inside said sheath, said probe terminating in a free end and including a cylindrical outer surface, a longitudinal channel formed in said probe, an opening on said surface proximate said free end, and an angled guide connecting said channel and said opening, and said guide being angled in a direction toward said free end, said probe being movable from a first, extended position wherein said free end projects from said sheath, to a second, retracted position wherein said free end is substantially disposed inside said sheath, said probe being spring biased to said first position;

placing said needle assembly on first tissue adjacent said site such that the closed end of the sheath is in contact therewith;

exerting sufficient force to move said sheath into its retracted position, thereby permitting said sharp cutting edge to penetrate said first tissue to a desired depth;

allowing said sheath to move back into its second, extended position;

threading a length of suture material through said channel, said guide and out said opening such that an end of said suture material projects therethrough;

positioning a trocar at second tissue adjacent said surgical site and penetrating said tissue to said desired depth with said trocar;

introducing a surgical snare through said trocar until said snare is disposed proximate said free end of the suture material;

capturing said end of said piece of suture material in said snare;

withdrawing said captured end of said piece of suture material through said second tissue;

withdrawing said needle assembly from said first tissue; and tying a knot in the piece of suture material by using said free end thereof.

9. The method of claim 8 wherein the step of introducing a suture snare through said trocar comprises the further step of introducing a resilient loop through said trocar.

10. The method of claim 8 comprising the further step of inserting the free end of the probe needle assembly into the snare prior to capturing the end of the piece of suture material in said snare.

* * * * *